(12) United States Patent
Joseph et al.

(10) Patent No.: US 7,641,777 B2
(45) Date of Patent: Jan. 5, 2010

(54) BIOLOGICAL TESTING SYSTEM

(75) Inventors: Abner D. Joseph, Carmel, IN (US);
Jack Schlanser, Indianapolis, IN (US)

(73) Assignee: Roche Diagnostics Operations, Inc.,
Indianapolis, MN (US)

( * ) Notice: Subject to any disclaimer, the term of this patent is extended or adjusted under 35 U.S.C. 154(b) by 863 days.

(21) Appl. No.: 10/935,522

(22) Filed: Sep. 7, 2004

(65) Prior Publication Data

US 2006/0052682 A1    Mar. 9, 2006

(51) Int. Cl.
*G01N 25/00* (2006.01)
*G01N 27/70* (2006.01)
*G01N 33/00* (2006.01)
*G01N 27/00* (2006.01)
*H01R 13/66* (2006.01)

(52) U.S. Cl. .................. 204/406; 204/403.1; 324/713; 436/95; 422/82.01; 439/620.01

(58) Field of Classification Search ............... None
See application file for complete search history.

(56) References Cited

U.S. PATENT DOCUMENTS

| | | |
|---|---|---|
| 2,802,188 A | 8/1957 | Badders |
| 3,899,234 A | 8/1975 | Yeater et al. |
| 3,980,376 A | 9/1976 | Rosen |
| 4,129,351 A | 12/1978 | Sugimoto et al. |
| 4,221,448 A | 9/1980 | Logerot et al. |
| 4,303,294 A | 12/1981 | Hamsher, Jr. et al. |
| 4,327,955 A | 5/1982 | Minter |
| 4,669,795 A | 6/1987 | Bonhomme |
| 4,696,529 A | 9/1987 | Verhoeven et al. |
| 4,713,020 A | 12/1987 | Awano et al. |
| 4,894,022 A | 1/1990 | Guckenheimer |
| 4,904,197 A | 2/1990 | Cabourne |
| 5,282,950 A | 2/1994 | Dietze et al. |
| 5,427,533 A | 6/1995 | Chambers |
| 5,502,396 A | 3/1996 | Desarzens et al. |
| 5,709,562 A | 1/1998 | Kourimsky |

(Continued)

FOREIGN PATENT DOCUMENTS

EP    0 327 060 A2    8/1989

(Continued)

*Primary Examiner*—Jill Warden
*Assistant Examiner*—Timothy G Kingan
(74) *Attorney, Agent, or Firm*—Woodard, Emhardt, Moriarty, McNett & Henry LLP

(57) ABSTRACT

A connector for establishing electrical connection between a testing device and a test strip with a biological fluid thereon includes a contact pad on the test strip, and one or more contact wires in the testing device. When the strip is inserted into the testing device, the end of the strip engages with a bight in the contact wire, pushing the contact wire in a direction normal to the direction of insertion. The movement of the contact wire forces a second portion of the wire against a part of the housing, thereby deforming the wire and moving another portion of the wire toward the contact pad. Some embodiments of the invention include 4, 6, 8, 15, or more contacts, which may be situated so as to receive the end of the test strip substantially simultaneously, or may be staggered in 2, 3, or more rows to spread out the resistance to movement presented.

2 Claims, 2 Drawing Sheets

U.S. PATENT DOCUMENTS

| | | |
|---|---|---|
| 5,722,845 A | 3/1998 | Debortoli et al. |
| 5,913,699 A | 6/1999 | Zielke |
| 6,015,311 A | 1/2000 | Benjamin et al. |
| 6,447,338 B1 | 9/2002 | Bricaud et al. |
| 6,454,607 B2 | 9/2002 | Bricaud |
| 2001/0016978 A1 | 8/2001 | Hamatani et al. |

FOREIGN PATENT DOCUMENTS

| | | |
|---|---|---|
| GB | 622 922 A1 | 5/1949 |

BIOLOGICAL TESTING SYSTEM

TECHNICAL FIELD OF THE INVENTION

The present invention relates to testing apparatus for testing the presence or concentration of one or more substances in a biological fluid, and more particularly to such a device that includes one or more electrical connections between a test strip (bearing a sample of the biological fluid) and a test meter.

BACKGROUND OF THE INVENTION

Measuring the concentration of substances, particularly in the presence of other substances, is important in many fields. This is especially true in medical testing and diagnosis. For example, the measurement of glucose in body fluids, such as blood, is crucial to the effective treatment of diabetes.

Multiple methods are known for measuring the concentration of analytes, for example glucose, in a blood sample. Such methods typically fall into one of two categories: optical methods and electrochemical methods. Optical methods generally involve reflectance or absorbance spectroscopy to observe the spectrum shift in a reagent. Such shifts are caused by a chemical reaction that produces a color change indicative of the concentration of the analyte. Electrochemical methods generally involve, alternatively, amperometric or coulometric responses indicative of the concentration of the analyte. See, for example, U.S. Pat. No. 4,233,029 to Columbus, U.S. Pat. No. 4,225,410 to Pace, U.S. Pat. No. 4,323,536 to Columbus, U.S. Pat. No. 4,008,448 to Muggli, U.S. Pat. No. 4,654,197 to Lilja et al., U.S. Pat. No. 5,108,564 to Szuminsky et al., U.S. Pat. No. 5,120,420 to Nankai et al., U.S. Pat. No. 5,128,015 to Szuminsky et al., U.S. Pat. No. 5,243,516 to White, U.S. Pat. No. 5,437,999 to Diebold et al., U.S. Pat. No. 5,288,636 to Pollmann et al., U.S. Pat. No. 5,628,890 to Carter et al., U.S. Pat. No. 5,682,884 to Hill et al., U.S. Pat. No. 5,727,548 to Hill et al., U.S. Pat. No. 5,997,817 to Crismore et al., U.S. Pat. No. 6,004,441 to Fujiwara et al., U.S. Pat. No. 4,919,770 to Priedel, et al., and U.S. Pat. No. 6,054,039 to Shieh, which are hereby incorporated in their entireties.

A sample-receiving portion of the testing apparatus typically controls the geometry of the blood sample. In the case of blood glucose meters, for example, the blood sample is typically placed onto or into a disposable test strip that is inserted into a test meter. In the case of electrochemical test meters, electrical signals must be transferred between the meter and the test strip and vice versa.

Test system designers desire to minimize the size of the sample required for accurate measurement in order to improve the user experience. The resulting test sensor and test strip miniaturization has resulted in the use of thin film test strip patterns comprised of noble metals deposited on plastic substrates, such as by plating and subsequent laser ablation, to form the electrodes and associated connector contact pads of the test strip. These techniques allow for improved edge quality and improved dimensional resolution of the metallized features on the test strip. Such thin film coatings are highly prone to scratching by current commercially available connectors. Therefore, reducing abrasion between the test strip contact pad and meter connector contact wire is especially important in biosensor designs. Repeat insertions of the test strip (two to four times) can render these thin film coated biosensors useless. Even the first-time insertion of the test strip into the test meter may cause some removal of these thin film coatings by the test meter connector. The result is a less reliable connection between the contact pad on a test strip and the connector contact wire in the test meter.

Reducing abrasion between the test strip contact pad and meter connector contact wire is also important for longevity of the test meter. A typical test meter may have a life cycle requirement of over 10,000 test strip insertions. During normal use, a single test strip may be inserted and removed from the meter several times before the test is successfully performed. Abrasive contact between the connector contact wire and contact pad can reduce the longevity of the test meter connector, thereby further reducing the reliability of the system. Some biosensor systems are designed for use by consumers, who sometimes put still further stresses on the test system by using the system in environments at the margins of its design specifications, such as in high-humidity environments, or exposing the device to air containing corrosive components.

Thus, there is a need for further contributions and improvements to biosensor system technology, including connectors that provide improved performance and resistance to abrasion of test strip contact pads and meter connector contact wires.

SUMMARY OF THE INVENTION

It is an object of the present invention to provide an improved connector for biosensor systems. It is a further object of the invention to provide a connector that is less subject to abrasion of contact pads and contact wires, and resulting reliability failures, than many prior art systems.

Some forms of the present invention improve user experience by increasing the probability of the test meter connector making a reliable contact with the inserted test strip. One form includes a system for measuring an analyte of interest in a biological fluid, where a connector provides an interface between a test strip bearing the biological fluid and a test meter. The analyte of interest is applied to a test strip having at least one contact pad for mating with the connector when the test strip is inserted through an opening in the meter housing. The connector comprises at least one contact wire disposed within the housing, where each contact wire has a distal portion and a proximal portion. The contact wire's proximal portion engages the connector housing and anchors the distal portion to the connector housing. The contact wire contacts the test strip only upon full insertion of the test strip into the test meter.

In another form of the invention, a connector for use in a test meter adapted to measure an analyte of interest in a biological fluid applied to a test strip having at least one contact pad for mating with the connector is disclosed, said connector comprising a housing having an opening therein for receiving the test strip when the test strip is moved in an insertion direction; and at least one contact wire disposed adjacent the opening, the contact having a proximal portion and a contact portion disposed between the proximal portion and the opening, the contact wire being disposed in relation to the opening such that insertion of the test strip in the insertion direction allows the test strip to pass adjacent the contact portion without touching the contact portion and initial engagement of the test strip with the contact wire occurs at the proximal portion, wherein insertion of the test strip into the opening in the insertion direction causes the test strip to push the proximal portion away from the test strip, and wherein further insertion of the test strip causes the contact wire to engage the housing and deflect therefrom, thereby pushing the contact portion toward the test strip and into engagement with the at least one contact pad.

In another form of the invention, a connector for use in a test meter adapted to measure an analyte of interest in a biological fluid applied to a test strip having at least one contact pad for mating with the connector is disclosed, said connector comprising a housing having a top portion and a bottom portion in substantially rigidly fixed spatial relationship and defining a slot therebetween; and at least one contact wire for establishing electrical contact with a respective one of the at least one contact pad of the test strip when the test strip is inserted into the slot, each at least one contact wire comprising a first portion, a second portion, and a third portion, wherein for each of the at least one contact wires, when the test strip is inserted through the slot, the test strip passes between the first portion and the housing bottom portion and does not touch the first portion; after passing the first portion, the test strip passes between and touches both the third portion of the contact wire and the bottom portion of the housing, the third portion of the contact wire moving away from the bottom portion of the housing and biasing the test strip toward the bottom portion of the housing; in response to the contact wire moving away from the bottom portion of the housing, the second portion of the contact wire applies a force to the housing top portion, and in response to the contact wire applying a force to the top portion of the housing, the contact wire is deformed so that the first portion of the contact wire contacts the respective at least one contact pad on the test strip.

In another form of the invention, a connector for use in a test meter adapted to measure an analyte of interest in a biological fluid applied to a test strip having at least one contact pad for mating with the connector is disclosed, said connector comprising a housing having a housing distal end and a housing proximal end; a slot formed in the housing distal end for receiving the test strip when the test strip is inserted into the housing in an insertion direction; a wire cavity defined within the housing and communicating with the slot; at least one contact wire disposed within the wire cavity for establishing electrical contact with a respective one of the at least one contact pad of the test strip when the test strip is inserted into the slot, each at least one contact wire disposed in the wire cavity and having a contact wire distal end, a contact wire proximal end, and a contact wire bight disposed between the contact wire distal end and the contact wire proximal end; wherein the wire cavity has a maximum height H measured in a direction substantially perpendicular to the test strip when the test strip is contained within the wire cavity; wherein each at least one contact wire in a quiescent state has a maximum total contact wire height C between the contact wire bight and the contact wire distal end; wherein the test strip has a test strip maximum height within the wire cavity of T; wherein H<C+T.

In another form of the invention, a testing system is disclosed, comprising: a housing; a connector disposed in the housing; and a test strip adapted for insertion into the connector, the test strip having at least one contact pad thereon; an electronic circuit adapted to produce an output signal corresponding to the presence or concentration of an analyte in a sample of bodily fluid that is in contact with the test strip inserted into the connector; the connector comprising at least one contact wire, each of the at least one contact wire configured such that when a test strip is inserted into the connector, the test strip exerts a force against the contact wire, the force deforming the contact wire against the housing to bring the contact wire into electrical communication with a contact pad on the test strip.

In another form of the invention, a testing system comprising a test meter adapted to measure an analyte of interest in a biological fluid applied to a test strip having at least one contact pad for mating with a connector disposed within the test meter is disclosed, said connector comprising: a housing having a housing distal end and a housing proximal end; a slot formed in the housing distal end for receiving the test strip when the test strip is inserted into the housing in an insertion direction; a wire cavity defined within the housing and communicating with the slot; at least one contact wire disposed within the wire cavity for establishing electrical contact with a respective one of the at least one contact pad of the test strip when the test strip is inserted into the slot, each at least one contact wire disposed in the wire cavity and having a contact wire distal end, a contact wire proximal end, and a contact wire bight disposed between the contact wire distal end and the contact wire proximal end; wherein the wire cavity has a maximum height H measured in a direction substantially perpendicular to the test strip when the test strip is contained within the wire cavity; wherein each at least one contact wire in a quiescent state has a maximum total contact wire height C between the contact wire bight and the contact wire distal end; wherein the test strip has a test strip maximum height within the wire cavity of T; wherein H<C+T.

DETAILED DESCRIPTION OF THE PREFERRED EMBODIMENTS

Figure 1:
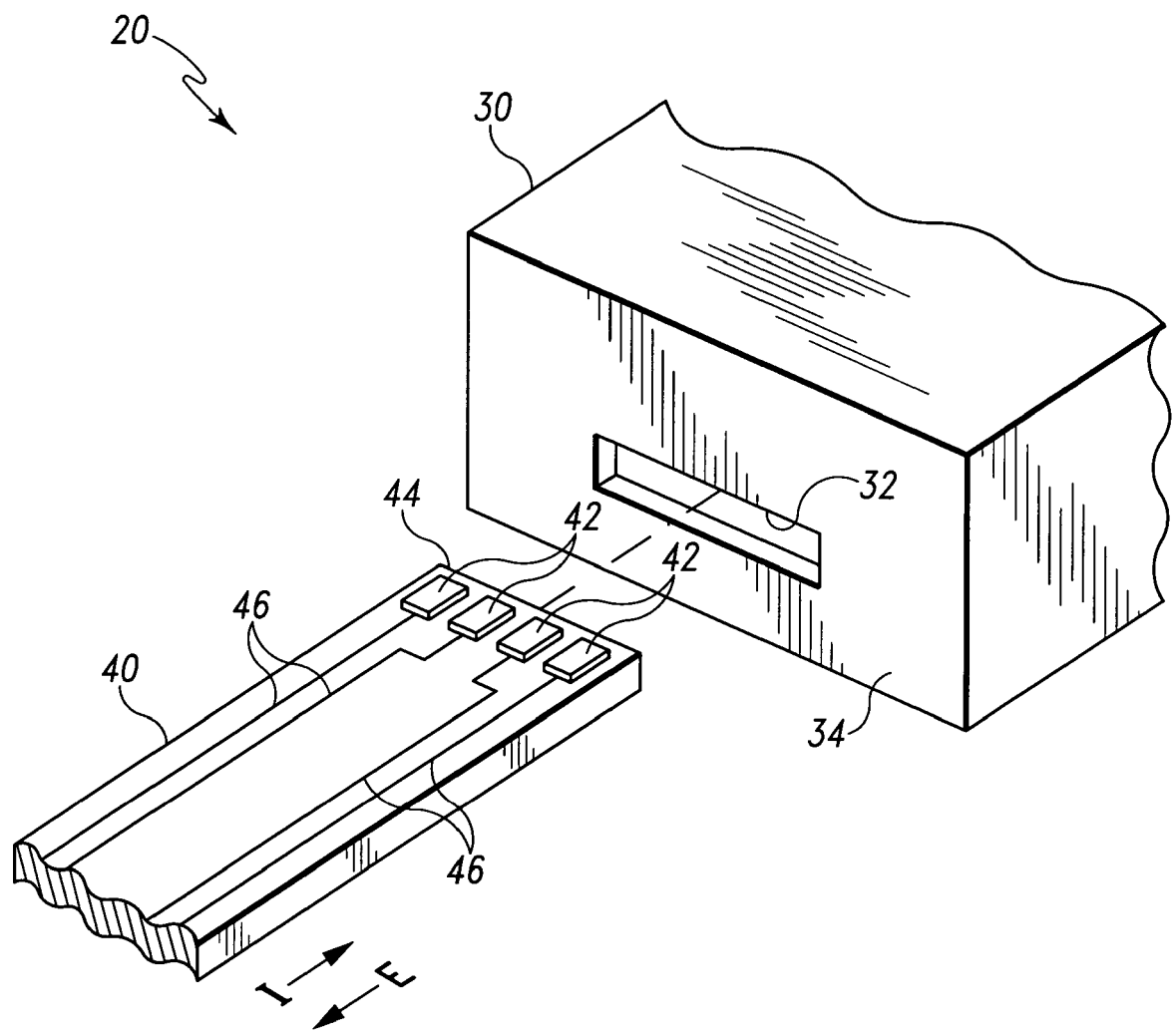
FIG. 1 is a perspective view of a biological testing system using one embodiment of the present invention.

For the purpose of promoting an understanding of the principles of the present invention, reference will now be made to the embodiment illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein are contemplated as would normally occur to one skilled in the art to which the invention relates.

This application incorporates by reference the applications titled SYSTEM AND METHOD FOR ANALYTE MEASUREMENT USING AC EXCITATION (U.S. Provisional Application No. 60/480,298, filed Jun. 20, 2003), METHOD OF MAKING A BIOSENSOR (case number BMID 9958 CIP US, filed Jun. 20, 2003), DEVICES AND METHODS RELATING TO ANALYTE SENSORS (U.S. Provisional Application No. 60/480,397, filed Jun. 20, 2003), and ELECTRODES, METHODS, APPARATUSES COMPRISING MICRO-ELECTRODE ARRAYS (U.S. patent application Ser. No. 10/264,891, filed Oct. 4, 2002), and U.S. Pat. No. 6,379,513 B1, which are hereby incorporated herein in their entireties.

The application of recent improvements in laser ablation techniques to the manufacture of medical test strips has significantly increased the resolution and fineness of metallized contact pad and connector trace geometries on test strips. This innovation has reduced the sample size required for accurate measurement of an analyte of interest in a biological fluid. However, these detailed and delicate structures are susceptible to abrasive damage. As a result, there is a need for less abrasive connection systems and techniques minimizing test strip abrasion during insertion and extraction. Embodiments of the present invention provide a significant improvement in this aspect of the art.

The present invention minimizes or eliminates abrasion of test strip contact pads formed of a thin layer of metal when the test strip is inserted into a test meter. Little or no damage to the test strip thin film surface by the connector, or to the connector contact wire by the test strip, will occur when using the present invention due to the non-contact insertion design of the present invention. Only after substantially full insertion of the test strip into the test meter does the connector contact wire come into contact with the test strip contact pad.

Generally, exemplary biological testing system 20 shown in FIG. 1 includes a reusable testing meter 30 having a distal end 34. A disposable test strip 40 is inserted in direction I through slot 32 in end 34. Strip 40 includes at least one contact pad 42 (four such contact pads are shown in FIG. 1 by way of example only) near its end 44. These contact pads are connected via conductors 46 to electrodes (not shown) near the end of strip 40 opposite end 44 (i.e., near the end in the direction indicated by extraction directional arrow E). As a non-limiting example, one embodiment has four contact pads connected to four electrodes. Other embodiments of the invention may include more or fewer contact pads, different numbers and patterns of conductor traces 46, and/or different numbers of electrodes on a given test strip 40. The test strip 40 is inserted into testing device 30 in insertion direction I.

Figure 2:
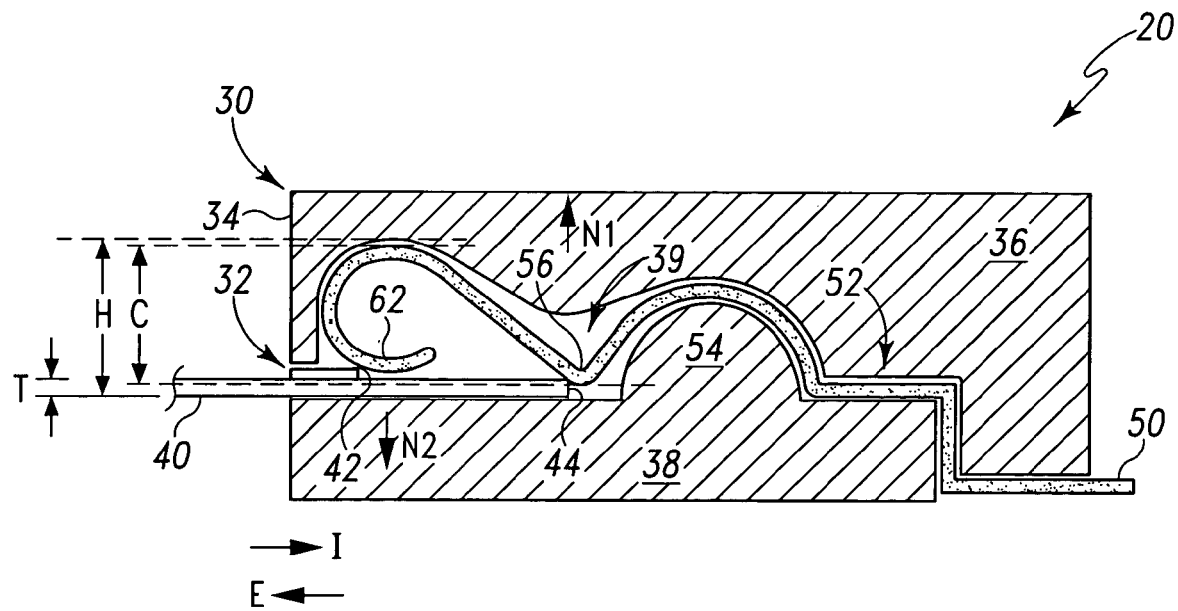
FIG. 2 is a cross-sectional view of the system shown in FIG. 1 at a point of time during insertion of the test strip.

Turning to FIG. 2, the biological testing system 20 is shown in cross-section. Testing meter 30 includes a connector for mating with test strip 40, the connector comprising upper connector housing portion 36 and lower connector housing portion 38, which are assembled into a substantially rigid spatial relationship. At least one connector contact wire 50 is captured between upper connector housing portion 36 and lower connector housing portion 38. In a preferred embodiment, upper connector housing portion 36 and lower connector housing portion 38 are formed from injection-molded plastic and are snapped together in order to form an assembled housing defining a wire cavity 39 capturing contact wire 50. In various embodiments, contact wire 50 can be formed by unplated or pre-plated drawn round or square wire, which is bent into the desired shape. As a non-limiting example, contact wire 50 may be made from cold drawn copper-based alloy that is plated with Ni followed by an overplating of hard Au, Pd or Pd-based alloys with a thin flash plating of Au. Alternatively, contact wires 50 may be formed from flat strip metal alloys which are stamped and formed into the desired shape and post-plated as described above.

Upper connector housing portion 36 and lower connector housing portion 38 together define a contact wire proximal end capturing section 52 and a test strip insertion limiting wall 54. When the upper connector housing portion 36 and lower connector housing portion 38 are assembled, contact wire 50 passes through the bends in area 52 and over rounded projection 54. In the embodiment of FIG. 2, the contact wire 50 proximal end is configured to allow surface mounting to a printed wiring board (PWB). In alternative embodiments, the contact wire 50 is oriented to allow for mounting into a plated through hole in a PWB for wave soldering.

Although FIG. 2 shows slot 32 formed by connector housing upper portion 36 and lower portion 38, other embodiments of the present invention contemplate slot 32 formed by a housing of test meter 30 and communicating with a separate opening in the connector housing. In order to use biological testing system 20, a test strip 40 is inserted into the slot 32 in insertion direction I. This causes the distal end of test strip 40 to enter the wire cavity 39. As test strip 40 is inserted, the leading end 44 of the test strip 40 passes under contact portion 62 of contact wire 50 without touching contact portion 62. This prevents contact wire 50 from abrading contact pad 42 as test strip 40 slides by contact portion 62.

Further insertion of the test strip 40 in the insertion direction I causes the distal end 44 of test strip 40 to come into contact with connector contact wire 50 at bight 56 formed in the contact wire 50. As test strip 40 is inserted further, interaction between test strip 40 and bight 56 of wire 50 begins to force contact wire 50 away from lower housing portion 38 in direction $N_1$, which is substantially normal to the direction of insertion I.

As used herein, H is the maximum height of the wire cavity 39 measured in a direction substantially perpendicular to the test strip 40, C is the maximum total vertical distance occupied by the contact wire 50 substantially perpendicular to the test strip 40 between the bight 56 and the distal end 34 of the connector 30, and T is the maximum vertical height of the test strip 40 within the wire cavity 39. In the preferred embodiment, H<C+T. The result of this height difference is that the test strip 40 cannot be fully inserted into the wire cavity 39 without compressing the contact wire 50.

Figure 3:
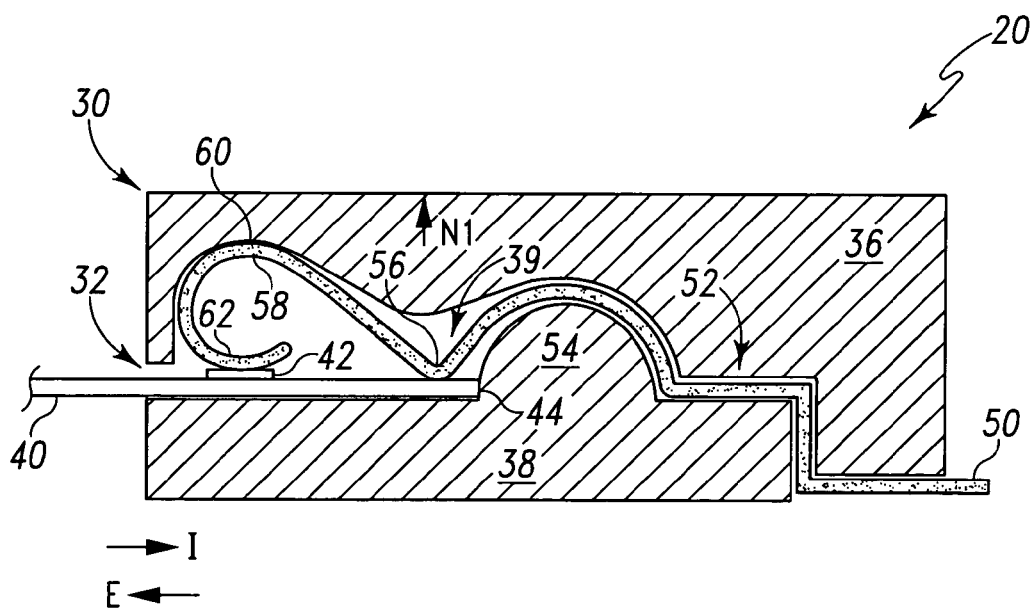
FIG. 3 is a cross-sectional view of the system of FIG. 1 after the test strip is fully inserted.

As shown in FIG. 3, insertion of test strip 40 proceeds in insertion direction I until test strip end 44 reaches test strip insertion limiting wall 54, where further insertion in the insertion direction I is prevented. By this point, the movement of contact wire 50 in the normal direction $N_1$ has caused contact wire portion 58 to move up as well and to come into contact with the lower surface of housing upper portion 36 at point 60, thereby applying a normal force to upper housing portion 36. This, in turn, causes a counter-force to be applied to the contact wire 50 in the normal direction $N_2$. Contact wire 50 is deformed at this point, causing contact portion 62 to move into electrical contact with contact pad 42 of test strip 40. In a preferred embodiment, contact wire 50 is shaped such that full insertion of the test strip 40 causes the contact wire 50 to be squeezed between test strip 40 and housing upper portion 36. It will be appreciated that in the preferred embodiment of the present invention, movement of contact wire regions 56 and 58 is normal to the insertion direction I of movement of test strip 40, and that the deformation of contact wire 50 brings contact wire contact portion 62 into contact with contact pad 42 through motion in a direction $N_2$ substantially normal to test strip movement in insertion direction I.

It will also be appreciated from the above description that the downward bias of contact wire 50 in the direction $N_2$ also forces contact wire 50 bight 56 into squeezing contact with distal end 44 of test strip 40, which will help to retain test strip 40 in its fully inserted position. Further, although there may be some friction between connector contact wire 50 and test strip 40 where test strip 40 rubs along contact wire bight 56, test strips 40 can be designed so that little or no contact metal is scraped off contact pad 42 or contact wire contact portion 62 in the process, since the electrical contact occurs at a point away from the sliding action at bight 56. Further, since the actual contact region 62 of contact wire 50 is removed from the contact wire contact portion 56 that incurs the frictional force, the contact portion 62 is in some embodiments specially treated to improve the contact, such as by plating the region with materials including, but not limited to, Pd, Ni, NiPd, NiCo, Sn, SnPb, Ag, Cu, Au, or German Silver, while the bight 56 of wire portion 50 can be specially treated to withstand the friction it experiences, even using coatings that do not conduct electricity well.

Certain variations on this embodiment include more or fewer contact pads and contact wires than the four shown herein. For examples, 2, 4, 6, 8, 15, 24 or other number of contacts may be "stacked" in the connector by placing substantially identical connector contact wires 50 side-by-side between the halves of the connector housing. In some of these embodiments, the wires are placed in a staggered arrangement of preferably two or three rows so that bight 58 of each contact wire 50 is initially engaged by the test strip 40 at a different moment than either of its immediate neighboring contact wires. This variation reduces the insertion force required to pass the test strip 40 under the contact wires 50, but allows the total force holding the test strip 40 in place (once it is fully inserted) to be the same as for single-row designs.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

All publications, prior applications, and other documents cited herein are hereby incorporated by reference in their entirety as if each had been individually incorporated by reference and fully set forth.

What is claimed is:

1. A method for connecting a test meter adapted to measure an analyte of interest in a biological fluid applied to a test strip having a contact pad, comprising:

a. providing a meter including a housing having a first wall and a second wall defining an opening therebetween, the housing further including an insertion limiting wall positioned for engagement by a test strip inserted into the opening, the meter further including a contact wire for establishing electrical contact between the test meter and the contact pad of the test strip when the test strip is inserted into the slot, the contact wire comprising first, second and third portions, the first portion for engaging the contact pad of the test strip, the third portion being for engaging the test strip at a location spaced from the contact pad, the contact wire having a first condition in which no test strip is received within the opening and in which:

the first portion is positioned adjacent to but spaced apart from the first wall, the test strip having a thickness and the first portion being located a distance from the first wall which is greater than the thickness of the test strip;

the second portion is positioned adjacent to the second wall, the third portion is positioned adjacent to the first wall at a distance which is less than the thickness of the test strip, b. partially inserting the test strip into the opening adjacent the first wall a first distance to a position in which the test strip is in contact with the third portion of the contact wire but is not in contact with the first portion of the contact wire, the third portion of the contact wire having been moved away from the first wall to a position more distant from the first wall than in the first condition of the contact wire; and c. fully inserting the test strip into the opening adjacent the first wall a second distance to a position in which the test strip is in engagement with the insertion limiting wall, the third portion of the contact wire having been moved away from the first wall to a position more distant from the first wall than when the test strip has been partially inserted into the opening, the first portion of the contact wire being in electrical contact with the contact pad of the test strip when the test strip is engaged with the insertion limiting wall thereby allowing measurement of an analyte of interest in a biological fluid.

2. The method of claim 1 in which the first portion is in electrical contact with the contact pad only after substantially full insertion of the test strip.

* * * * *

UNITED STATES PATENT AND TRADEMARK OFFICE
CERTIFICATE OF CORRECTION

| | | |
|---|---|---|
| PATENT NO. | : 7,641,777 B2 | Page 1 of 1 |
| APPLICATION NO. | : 10/935522 | |
| DATED | : January 5, 2010 | |
| INVENTOR(S) | : Abner David Joseph | |

It is certified that error appears in the above-identified patent and that said Letters Patent is hereby corrected as shown below:

Title page 1, item 73 under the "Assignee" section, please change the assignee address to read --Indianapolis, IN (US)--.

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,641,777 B2  Page 1 of 1
APPLICATION NO. : 10/935522
DATED : January 5, 2010
INVENTOR(S) : Joseph et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1294 days.

Signed and Sealed this

Sixteenth Day of November, 2010

David J. Kappos
*Director of the United States Patent and Trademark Office*